United States Patent [19]

Sharif

[11] Patent Number: 5,466,846
[45] Date of Patent: Nov. 14, 1995

[54] PROCESS FOR PREPARATION OF STABLE AQUEOUS SOLUTIONS OF ZIRCONIUM CHELATES

[75] Inventor: Sharif Sharif, El-Kaherah, Egypt

[73] Assignee: Benchmark Research and Technology, Inc., San Antonio, Tex.

[21] Appl. No.: 340,661

[22] Filed: Nov. 16, 1994

[51] Int. Cl.$^6$ ..................................................... C07F 7/00
[52] U.S. Cl. ................................................................ 556/55
[58] Field of Search ................................................. 556/55

[56] References Cited

U.S. PATENT DOCUMENTS

| | | | |
|---|---|---|---|
| 4,460,751 | 7/1984 | Hanlon et al. | 525/371 |
| 4,477,360 | 10/1984 | Almond | 252/8.551 |
| 4,692,254 | 9/1987 | Kucera | 252/8.551 |
| 4,958,038 | 9/1990 | Smeltz | 556/55 |
| 5,076,847 | 12/1991 | Kay et al. | |
| 5,182,408 | 1/1993 | Sharlf | 556/55 |

FOREIGN PATENT DOCUMENTS 1093465  12/1967  United Kingdom .

*Primary Examiner*—Porfirio Nazario-Gonzalez
*Attorney, Agent, or Firm*—Donald R. Comuzzi; Christopher L. Makay

[57] ABSTRACT

Aqueous solutions of zirconium chelates are prepared by combining an alpha-hydroxycarboxylic acid salt with a solution of a zirconium compound. That preparation first involves formulating an alpha-hydroxycarboxylic acid salt through a stoichiometric reaction between an alpha-hydroxycarboxylic acids and a base. The stoichiometric reaction product consists of an approximately neutral solution of a corresponding alpha-hydroxycarboxylic acid salt. The alpha-hydroxycarboxylic acid salt is then added to a solution of a zirconium compound to produce a mildly acidic or basic solution of the corresponding zirconium alpha-hydroxycarboxylic chelate. Alternatively, the alpha-hydroxycarboxylic acid salt may be pre-prepared and added in solid or liquid form to the zirconium compound before the zirconium compound is placed in solution so that the corresponding zirconium alpha-hydroxycarboxylic chelate is produced.

10 Claims, No Drawings

PROCESS FOR PREPARATION OF STABLE AQUEOUS SOLUTIONS OF ZIRCONIUM CHELATES

BACKGROUND OF THE INVENTION

1. Field of the Invention

The present invention relates to a process for the preparation of stable aqueous solutions of zirconium chelates at 100% chemical yield without effluent or solid waste. The aqueous zirconium chelate solutions remain stable upon aging, boiling, or dilution and also after the addition of acids and/or bases.

2. Description of the Related Art

Chelates are utilized in the paper coating industry as starch and protein insolubilizers and in the petroleum industry for fracturing petroleum bearing formations. Chelates are used in both aqueous and non-aqueous solutions to retain metals in solution at high temperatures and over wide pH ranges so that the metals remain compatible with other chemicals. Chelates can be formed of transition metals such as titanium, zirconium, copper, iron, and the like and also aluminum and boron.

Particularly in the petroleum industry, chelates are employed in cross-linking gels such those disclosed by Almond in U.S. Pat. No. 4,477,360. Almond discloses an aqueous gel containing a retarded cross-linking composition of a zirconium salt or chelate and polyhydroxyl containing compounds. Almond further discloses that the polyhydroxyl containing compounds be admixed with an aqueous fluid and a cross-linking compound featuring zirconium chelates. These compositions are typically referred to as polyols, examples of which include glycerol, erythritol, threitol, and ribitol. The gelling agents employed by Almond include guar gum, locust bean gum, karaya gum, sodium carboxymethylguar and several other compounds of guar.

Smeltz, U.S. Pat. No. 4,958,038 issued Sep. 18, 1990, discloses a process which comprises combining glycerol, erythritol, arabitol, etc. and lactic acid, glycolic acid, malic acid, citric acid, tartaric acid, saccharic acid, gluconic acid, glyceric acid or mandelic acid to provide an aqueous solution of polyol and alpha-hydroxy carboxylic acid, and then at an alkaline pH of 10 or less reacting the solution with a titanium compound of an inorganic acid at an alpha-hydroxy carboxylic acid to titanium mol ratio between 0.5 to 1 and about 4 to 1 and a polyol to titanium mol ratio between about 0.25 to 1 and about 2 to 1. In fracturing formations, Smeltz uses solvatable polysaccharides which include guar gum and locust bean gum, as well as other galactomannan and glucomannam gums, such as those derived from sennas, Brazilwood, Tera, Honey locust, Karaya gum and the like.

Hanlon, et. al., U.S. Pat. No. 4,460,751 describes a crosslinker which is made by preparing an alpha-hydroxy carboxylic acid solution, then adding a zirconium compound, e.g. zirconium oxychloride to form a second mixture, and finally adds the amine compound to the mixture. If zirconium carbonate is used, the zirconium carbonate is added to water to form a first mixture, next the amine compounded is added to form a second mixture, and finally the alpha-hydroxy carboxylic acid is added to the second mixture.

Examples of the previous nonadvantageous methods of preparing zirconium chelates involves the use of dangerous solvents, such as ethers and alcohols, for producing zirconium triethanolamine chelates via zirconium n-propyl or n-butyl zirconate solubilized in n-propanol. This method involves the soluablization of zirconium tetrachloride which is also a dangerous chemical in n-propanol or ether followed by reacting it with triethanolamine. See Kucera, U.S. Pat. No. 4,692,254 describing such methods in detail.

Also aqueous chelates are produced through the separation of insoluble chelates as intermediates such as zirconium citrate, zirconium lactate and zirconium tartrate. This process generates effluents such as sodium sulphate, ammonium sulphate and other anions such as chlorides, nitrates, etc. See Van Mater, U.S. Pat. No. 2,498,514 describing such methods in more detail.

The prior methods of preparing zirconium chelates for preparation of solutions useful in fracturing oil and gas strata have encountered such problems as low chemical yield, a need for an organic solvent which causes fire hazard and may produce toxic fumes or exhibits poor stability on aging and/or dilution, exposure to the atmospheric condition, dilution with water, boiling and/or the addition of inorganic acids or bases. Also, such prior preparation methods have generated organic and/or inorganic effluent and/or solid waste.

SUMMARY OF THE INVENTION

In accordance with the present invention, aqueous solutions of zirconium chelates are prepared by combining an alpha-hydroxycarboxylic acid salt with a solution of a zirconium compound. That preparation first involves formulating an alpha-hydroxycarboxylic acid salt through a stoichiometric reaction between an alpha-hydroxycarboxylic acids and a base. The stoichiometric reaction product consists of an approximately neutral solution of a corresponding alpha-hydroxycarboxylic acid salt. The alpha-hydroxycarboxylic acid salt is then added to a solution of a zirconium compound to produce a mildly acidic or basic solution of the corresponding zirconium alpha-hydroxycarboxylic chelate. Alternatively, the alpha-hydroxycarboxylic acid salt may be pre-prepared and added in solid or liquid form to the zirconium compound before the zirconium compound is placed in solution so that the corresponding zirconium alpha-hydroxycarboxylic chelate is produced.

It is, therefore, an object of the present invention to provide a novel process for preparing aqueous zirconium chelate solutions.

It is another object of the present invention to produce aqueous zirconium chelate solutions that remain stable upon aging, boiling, or dilution and also after the addition of acids and/or bases.

It is a further object of the present invention to produce aqueous zirconium chelate solutions that are useful in a wide range of industrial applications, especially in the areas of the paper coating industry and fracturing solutions for treating underground oil or gas bearing strata.

Still other objects, features, and advantages of the present invention will become evident to those skilled in the art in light of the following.

DETAILED DESCRIPTION OF THE PREFERRED EMBODIMENT

Aqueous solutions of zirconium chelates are prepared by combining an alpha-hydroxycarboxylic acid salt with a solution of a zirconium compound. Solutions of zirconium compounds suitable for use in the preparation of the aqueous solutions of zirconium chelates include, but are not limited to, zirconium basic sulfate, zirconium orthosulfate, zirconium sulfate, zirconium hydroxychloride, zirconium oxychloride, zirconium oxynitrate, zirconium hrdroxynitrate, ammonium zirconium carbonate, zirconium acetate, zirconium oxybromide, zirconium hydroxybromide, and mixtures thereof.

Alpha-hydroxycarboxylic acid salts utilized in the preparation of the aqueous solutions of zirconium chelates are the reaction products of an alpha-hydroxycarboxylic acid and a base. Alpha-hydroxycarboxylic acids suitable for use in the preparation of the alpha-hydroxycarboxylic acid salt include, but are not limited to, lactic acid, citric acid, tartaric acid, and mixtures thereof. Bases suitable for use in the preparation of the alpha-hydroxycarboxylic acid salt include, but are not limited to, ammonium; ammonium derivatives such as methyl ammonium, dimethyl ammonium, and hydroxyethyl ammonium; water soluble amines or amine derivatives such as triethanolamine, triisopuopanolamine, and diisopropylamine; and mixtures thereof or alkali metal carbonates, alkali metal bicarbonates, alkali metal hydroxides such as sodium hydroxide and potassium bromide, and mixtures thereof.

The preparation of an aqueous solution of a zirconium chelate first involves formulating an alpha-hydroxycarboxylic acid salt through a stoichiometric reaction between one of the above-described alpha-hydroxycarboxylic acids and one of the above-described bases. The stoichiometric reaction product consists of an approximately neutral solution of the corresponding alpha-hydroxycarboxylic acid salt (i.e., alkali metal or ammonium, ammonium derivative, amine, and amine derivative alpha-hydroxycarboxylic acid salt). The alpha-hydroxycarboxylic acid salt is then added to a solution of a zirconium compound to produce a mildly acidic or basic solution of the corresponding zirconium alpha-hydroxycarboxylic chelate. Alternatively, the alpha-hydroxycarboxylic acid salt may be pre-prepared and added in solid or liquid form to the zirconium compound before the zirconium compound is placed in solution so that the corresponding zirconium alpha-hydroxycarboxylic chelate is produced.

It should be noted that the claimed processes have 100% chemical yield and do not generate either organic and/or inorganic effluent and/or solid waste. The process utilizes only aqueous chemicals to produce purely aqueous products that eliminate the need for organic solvents and the attendant fire hazards and other disadvantages.

EXAMPLE 1

Preparation of triethanolamine zirconium lactate from ZBS (i) 246.4g of 99% triethanolamine is reacted with 238.9g of 88% lactic acid.

(ii) 256.0g of ZBS which contains 40% $ZrO_2$ is gradually added to the above triethanolamine lactate salt solution.

(iii) The reaction batch is mixed till a completely clear solution of zirconium triethanolamine lactate is obtained. The pH of the solution is about 6.0–6.5.

(iv) Dilute the product with 400g of dilute deionized water.

(v) The above aqueous chelate solution contains 9.0% $ZrO_2$ and is stable on aging for at least one year.

EXAMPLE 2

Preparation of triethanolamine zirconium lactate from ZOS (i) 985.6 g of triethanolamine is reacted with 238.9 g of 88% lactic acid.

(ii) 310.3 g of ZOS which contains 33% $ZrO_2$ is gradually added to the above triethanolamine lactate solution.

(iii) The reaction batch is mixed till a completely clear solution of zirconium triethanolamine lactate is obtained.

(iv) Dilute the above product with 300g of deionized water. The obtained solution has 5.6% $ZrO_2$.

(v) The final product has a pH of 7.8 and is stable on aging for at least one year.

EXAMPLE 3

Preparation of sodium zirconium lactate from ZBS (i) Add 500 g of deionized water to 460.6 g of 88% lactic acid.

(ii) React 360.0 g. of 50% NaOH with the above lactic acid solution.

(iii) To the above sodium lactate solution, add 500 g of ZBS. A slurry is obtained. pH is 4.9.

(iv) While mixing, add 73 g of 25% NaOH. Mix till a clear solution is obtained.

(v) Dilute the above solution with 963.5 g of deionized water.

(vi) The obtained product has a pH of 7.2 and contains 7.0% $ZrO_2$. It is stable on aging for at least one year.

EXAMPLE 4

(i) In 2000 ml glass beaker 818.9 g of 88% lactic acid was weighed out. The beaker was placed on a magnetic stirrer and the lactic acid was agitated using a magnetic bar.

(ii) Gradually 485.7g of ammonium hydroxide solution was added to prepare of ammonium lactate. In this mixture the $NH_3$ to lactate molar ratio is 1.0 to 1.0, based on 88% acid and 28.0% $NH_3$ in the lactic acid and the ammonium hydroxide solution, respectively. This neutralization reaction is exothermic and the addition of the ammonium hydroxide solution must be slow enough to avoid any boil-over. The temperature of the produced ammonium lactate solution was between 150–200 degrees F.

(iii) In a 4000 ml glass beaker 1000 g of zirconium chloride hydroxide solution was weighed and mixing was started. Gradually, the above hot ammonium lactate solution was added to the zirconium chloride hydroxide solution while mixing. After all of the ammonium lactate solution was added, the solution was mixed for an additional 15 minutes. When the reaction batch was cooled to room temperature, its pH was between 5.0–7.0 at this stage of the preparation. The temperature of the ammonium lactate solution before its addition to zirconium chloride hydroxide has been found to have no effect on the quality of the product.

(iv) The produced intermediate was almost a neutral solution of ammonium zirconium lactate which assays 8.7% $ZrO_2$ at a lactate to Zirconium molar ratio of 5.0 to 1.0.

The obtained product was stable on boiling, aging, dilution and when its pH was altered (by the addition of HCl or ammonium hydroxide) in the range of 3.0–10.0. The lactate to Zirconium molar ratio was 5.0 to 1.0.

EXAMPLE 5

(i) In a suitable beaker 315.2 g of sodium citrate dihydrate was dissolved in 598.4 g of distilled water and a clear solution was obtained. This solution of sodium citrate can also be obtained by mixing sodium hydroxide solution with citric acid solution or citric acid solids with sodium hydroxide solution or by mixing sodium hydroxide solids with citric acid solution.

(ii) The above sodium citrate solution was added to 500 g of zirconium hydroxychloride solution which contains 20.0% $ZrO_2$. The reaction batch was mixed continuously while the sodium citrate was being added. A clear solution of sodium zirconium citrate was obtained after the addition of sodium citrate solution was completed. The pH of the solution product was 6.2.

(iii) 23 g of 50% sodium hydroxide was added to raise the product pH to 9.0. The citrate to Zirconium molar ratio in this product was 1.34 to 1.00. The product contained 7.0% $ZrO_2$ and was stable on boiling, aging and dilution to very low $ZrO_2$ concentrations.

The starting zirconium material in the above two examples, examples (4) and (5), was zirconium hydroxychloride, however, any one or mixtures of the following zirconium chemicals may be used:

(i) Zirconium Oxychloride
(ii) Zirconium Oxynitrate
(iii) Zirconium Hydroxynitrate
(iv) Ammonium Zirconium Carbonate
(v) Zirconium Acetate
(vi) Zirconium Oxybromide
(vii) Zirconium Hydroxybromide
(viii) Zirconium Basic Carbonate
(ix) Zirconium Basic Sulfate
(x) Zirconium Orthosulfate
(xi) Zirconium Sulfate Also a mixture of zirconium hydroxychloride and any or all of the above zirconium starting materials can be used in the preparation of similar products.

EXAMPLE 6

(i) In a suitable beaker 630 gm of sodium citrate dihydrate was dissolved in 1196 gm of distilled water.

(ii) The above sodium citrate solution was added to 1000 gm of zirconium oxychloride solution which contained 20% of $ZrO_2$. A clear solution with a pH of 5.3 was obtained.

(iii) 104 gm of 50% sodium hydroxide was added while mixing to raise the product pH to 9.0. $ZrO_2$ content in the product was 6.8%. Good stability of the obtained solution was observed on boiling, aging, dilution and the addition of acids and bases to alter the pH between 3.0 and 10.0. The citrate to Zirconium molar ratio in this product was 1.34 to 1.00.

The alpha-hydroxy carboxylic acid to Zirconium molar ratio can vary between 0.5–20.0 to 1.0 and the $ZrO_2$ concentration in the products using these methods can vary between 0.5–17%.

EXAMPLE 7

(i) 97.1 gm of 28% ammonium hydroxide solution was mixed with 163.8 gm of 88% lactic acid to prepare ammonium lactate solution.

(ii) The above ammonium lactate solution was added to 500 gm of zirconium hydroxychloride solution which contains 20% $ZrO_2$ while mixing. A clear solution with a pH of 4.3 was obtained.

(iii) 154 gm of 28% ammonium hydroxide solution was added to establish a pH of 9.0 in the final solution product. The $ZrO_2$ content in the product was 10.9%. This ammonium zirconium lactate solution was stable on boiling, aging, dilution and the addition of bases and acids to alter the pH between 3.0–10. The lactate to Zirconium molar ratio was 2.0 to 1.0.

EXAMPLE 8

(i) In a suitable beaker 120 gm of granular tartaric acid was dissolved in 300 gm of distilled water.

(ii) 359 gm of 25% potassium hydroxide solution was mixed with the above tartaric acid solution to prepare potassium tartrate solution.

(iii) The above potassium tartrate solution was added to 500 gm of zirconium hydroxychloride solution which contains 20% $ZrO_2$ while mixing.

(iv) After the addition of the potassium tartrate solution was completed a clear solution of potassium zirconium tartrate was obtained. The pH of the product was 4.0 and it contains 7.8% $ZrO_2$. The tartrate to Zirconium molar ratio in the product was 1.0 to 1.0.

EXAMPLE 9

(i) In a suitable beaker 1809 gm of triethanolamine was mixed with 219 gm of 88% lactic acid.

(ii) The blend from (i) of this example was then added to 445 gm of zirconium oxynitrate which contains 20% $ZrO_2$ while mixing.

(iii) After the addition of lactic acid-triethanolamine blend was completed, a clear and stable solution of triethanolamine zirconium lactate was obtained.

(iv) pH of the product was 8.2, had 3 to 1 lactate to Zirconium molar ratio and contained 3.6% $ZrO_2$.

EXAMPLE 10

(i) 189 gm of 88% lactic acid was mixed with 122 gm of 50% sodium hydroxide solution to prepare sodium lactate solution.

(ii) The above sodium lactate solution was added to 510 gm of zirconium hydroxychloride solution which contains 15.2% $ZrO_2$ while mixing.

(iii) After the addition of the sodium lactate was completed a clear solution of sodium zirconium lactate was obtained. pH of the product was 5.8, contained 9.5% $ZrO_2$ and had a lactate to Zirconium molar ratio of 3.0 to 1.0.

EXAMPLE 11 pH of the product from Example 7 was increased to 10.0 by the addition of 50% NaOH to yield stable high pH solution of sodium zirconium lactate at a lactate to Zirconium molar ratio of 3.0 to 1.0.

EXAMPLE 12 pH of the product from Example 7 was lowered to 3.0 by the addition of hydrochloric acid to yield a stable, low pH product at a lactate to Zirconium molar ratio of 3.0 to 1.0.

EXAMPLE 13

755.9 gm of 28% ammonium hydroxide solution was added to 409.5 gm of 88% lactic acid to prepare sodium lactate solution.

The produced sodium lactate solution was added to 500 gm of zirconium oxynitrate solution which contained 20.0% $ZrO_2$, while mixing. A clear solution product of sodium zirconium lactate was obtained. The product had a pH of 7.5 and it contained 6.0% ZrO. The lactate to zirconium molar ratio in the solution product was 5.0 to 1.0.

The product was stable on the addition of acids or bases, dilution, boiling and/or aging.

EXAMPLE 14

506.9 gm of 28% ammonium hydroxide solution was added to 409.5 gm of 88% lactic acid to prepare ammonium lactate solution.

The above ammonium lactate solution was added to 500 gm of zirconium hydroxynitrate solution which contained 20.0% ZrO2. A clear and stable solution of ammonium zirconium lactate was obtained. The solution product had a pH of 5.3 and it contained 7.0% $ZrO_2$. The lactate to zirconium molar ratio in the product was 5.0 to 1.0.

The product was stable on the addition of acids or bases, dilution, boiling, and/or aging.

EXAMPLE 15

396.9 gm of 50% sodium hydroxide solution was added to 410 gm of 88% lactic acid to prepare sodium lactate solution.

The above sodium lactate solution was added to 500 gm of zirconium hydroxynitrate which contains 20.0% $ZrO_2$. A stable solution of sodium zirconium lactate with a pH of 10.4 was obtained. The product had a lactate to zirconium molar ratio of 5.0 to 1.0 and it was stable on the addition of acids and bases, dilution, boiling, and/or aging. The solution product was assayed 7.0% $ZrO_2$.

EXAMPLE 16

80.7 gm of 50% sodium hydroxide solution was added to 103.3 gm of 88% lactic acid to prepare sodium lactate solution.

The above solution was added to 230 gm of zirconium acetate solution which contained 22.0% $ZrO_2$, while mixing. A stable solution of sodium zirconium lactate with a pH of 6.2 was obtained. The solution product assayed 12.2% $ZrO_2$ and it was stable on the addition of acids or bases, dilution, boiling, and/or aging. The lactate to zirconium molar ratio in the product was 2.5 to 1.0.

The methods set forth in the foregoing examples are used to make the following list of chelates:

Zirconium Triethanolamine Lactate
Triethanolamine Zirconium Lactate
Sodium Zirconium Lactate
Sodium Zirconium Tartrate
Sodium Zirconium Glycolate
Sodium Zirconium Maliate
Sodium Zirconium Saccarate
Sodium Zirconium Gluconate
Sodium Zirconium Glycerate
Sodium Zirconium Mandelate
Ammonium Zirconium Citrate
Potassium Zirconium Glycolate
Potassium Zirconium Maliate
Potassium Zirconium Saccharate
Potassium Zirconium Gluconate
Potassium Zirconium Glycerate
Potassium Zirconium Mandelate
Amine (or amine derivative) Zirconium Citrate
Amine (or amine derivative) Zirconium Tartrate
Amine (or amine derivative) Zirconium Glycolate
Amine (or amine derivative) Zirconium Maliate
Amine (or amine derivative) Zirconium Saccharate
Amine (or amine derivative) Zirconium Gluconate
Amine (or amine derivative) Zirconium Glycerate
Amine (or amine derivative) Zirconium Mandelate The compositions obtained by the methods disclosed above are highly stable on boiling, aging, dilution to low $ZrO_2$ concentrations, and maintain stability over a pH range of 3 to 10.

Although certain preferred embodiments of the invention have been described herein for illustration, it will be appreciated that various modifications and changes of the procedures and compositions recited may be implemented without departing from the principles. Such changes are therefore deemed to lie within the scope and spirit of the invention except as may be necessarily limited by the appended claims.

I claim:

1. A method of preparing solutions of aqueous zirconium chelates, comprising:
   a. reacting ammonium hydroxide, sodium hydroxide, potassium hydroxide, water soluble amines or amine derivatives or alkali metal carbonates or bicarbonates with an alpha hydroxy carboxylic acid to prepare substantially neutral solutions of the corresponding alpha-hydroxycarboxylic salt;
   b. adding said alpha-hydroxycarboxylic salt to a slurry of zirconium basic sulfate or a solution of zirconium orthosulfate or zirconium sulfate and mixtures thereof to form a zirconium chelate.

2. The method of claim 1 wherein stoichiometric quantities of the reactants are used to produce zirconium chelates.

3. The method of claim 1 wherein the zirconium chelate has a pH in the range of 3 to 10.

4. The method of claim 1 wherein the alpha-hydroxy carboxylic acid to zirconium molar ratio is between 0.5–20 to 1.0.

5. The method of claim 1 wherein the zirconium dioxide concentration is from 0.5 to 17 percent.

6. A method of preparing zirconium chelates which comprises:
   a. dissolving an alpha-hydroxycarboxylic salt of sodium, potassium, ammonia or a water soluble amine or amine derivative in water to form clear solution; and
   b. adding said alpha-hydroxycarboxylic salt while mixing to a slurry of zirconium basic sulfate or a sloution of zirconium orthosulfate or zirconium sulfate and mixtures thereof to form a zirconium chelate.

7. The method of claim 6 wherein stoichiometric quantities of the reactants are used to produce zirconium chelates.

8. The method of claim 6 wherein the zirconium chelate has a pH in the range of 3 to 10.

9. The method of claim 6 wherein the alpha hydroxy carboxylic acid to zirconium molar ratio is between 0.5–20 to 1.0.

10. The method of claim 6 wherein the zirconium dioxide concentration is from 0.5 to 17 percent.

* * * * *